(12) United States Patent  (10) Patent No.: US 6,608,207 B2
Hijikata  (45) Date of Patent: Aug. 19, 2003

(54) PROCESS FOR PRODUCING SUBSTITUTED ALKYLAMINE DERIVATIVE

(75) Inventor: Chikara Hijikata, Shizuoka (JP)

(73) Assignee: Ihara Chemical Industry Co., Ltd., Tokyo (JP)

(*) Notice: Subject to any disclaimer, the term of this patent is extended or adjusted under 35 U.S.C. 154(b) by 0 days.

(21) Appl. No.: 09/980,255
(22) PCT Filed: Apr. 2, 2001
(86) PCT No.: PCT/JP01/02848
§ 371 (c)(1),
(2), (4) Date: Mar. 18, 2002
(87) PCT Pub. No.: WO01/74794
PCT Pub. Date: Oct. 11, 2001

(65) Prior Publication Data
US 2003/0028032 A1 Feb. 6, 2003

(30) Foreign Application Priority Data
Apr. 3, 2000 (JP) ......................................... 2000-100466

(51) Int. Cl.[7] ............................................. C07D 277/62
(52) U.S. Cl. ....................................................... 548/179
(58) Field of Search ......................................... 548/179

(56) References Cited

U.S. PATENT DOCUMENTS 6,197,969 B1 * 3/2001 Umezu et al. .............. 548/152

FOREIGN PATENT DOCUMENTS

JP       8-325235     12/1996
WO      99/16759      4/1999

OTHER PUBLICATIONS

Oya, M. et al.; "Acylation Reactions by Using N–Carboxy Amino Anhydride", Yuki Gosei Kagaku Kaishi; 29 (8), pp. 751 to 759 (1971), pp. 752 to 754.

* cited by examiner

Primary Examiner—Joseph K. McKane
(74) Attorney, Agent, or Firm—Kubovcik & Kubovcik

(57) ABSTRACT

The present invention lies in a process for producing a substituted alkylamine derivative represented by formula (3):

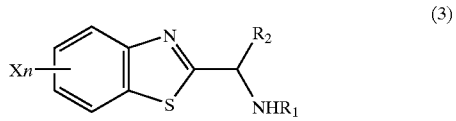

(3)

(wherein X is halogen, alkyl, alkoxy, cyano or nitro; n is an integer of 1 to 4; and $R_1$ and $R_2$ are each independently hydrogen or phenyl substituted or unsubstituted alkyl and may together form a 5- or 6-membered ring) or an acid addition salt thereof, which process comprises adding a salt of a 2-aminothiophenol derivative represented by formula (1):

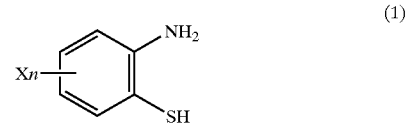

(1)

into an acid to allow the system to have a pH of 6 or less and convert the salt into a free 2-aminothiophenol of formula (1) and then reacting the 2-aminothiophenol derivative with an amino acid-N-carboxyanhydride represented by formula (2):

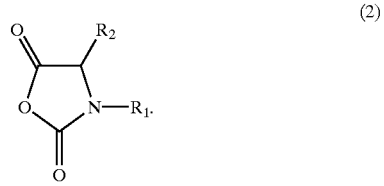

(2)

12 Claims, No Drawings

PROCESS FOR PRODUCING SUBSTITUTED ALKYLAMINE DERIVATIVE

This application is a 371 of PCT/JP01/02848 filed Apr. 2, 2001.

TECHNICAL FIELD

The present invention relates to a process for producing a substituted alkylamine derivative useful as an intermediate for medicine or agricultural chemical. More particularly, the present invention relates to a process for producing a substituted alkylamine derivative or an acid addition salt thereof from a 2-aminothiophenol derivative at a satisfactory yield industrially.

BACKGROUND ART 1-(2-benzothiazolyl)alkylamine derivatives have been known as substituted alkylamine derivatives each having a condensed heterocyclic ring. As a method for synthesis thereof, there is known a condensation reaction between a 2-aminothiophenol derivative and an amino acid-N-carboxyanhydride (see JP-A-8-325235). This method, however, has had a problem in that particular compounds such as (RS)-1-(6-fluoro-2-benzothiazolyl)ethylamine and the like are impossible to produce at a satisfactory yield. The method has further had problems in that the 2-aminothiophenol derivative used as a raw material has a strong odor of hydrogen sulfide and is unstable in the air; in particular, a fluorine-substituted 2-aminothiophenol derivative has a very strong odor, is unstable in such an extent that the derivative forms a disulfide easily even when the air is cut off, and is difficult to handle industrially; and yet use of such a compound is inevitable.

The 2-aminothiophenol derivative used as a raw material in the above reaction can ordinarily be produced easily at a high yield by hydrolyzing a substituted benzothiazole derivative with an alkali metal hydroxide such as potassium hydroxide or the like; in this case, however, the product is obtained as an alkali metal salt and shows alkaline. Meanwhile, the amino acid-N-carboxyanhydride also used as a raw material in the above reaction decomposes easily in the presence of an alkali to become an oligomer. Therefore, the 2-aminothiophenol derivative alkali metal salt synthesized in the above method need be made neutral or acidic. However, when hydrochloric acid or the like is added to the 2-aminothiophenol derivative alkali metal salt to convert the salt into a free 2-aminothiophenol derivative, a disulfide is formed, making very low the yield of the intended product.

For betterment scheme of the above problem, it was found out that a 1-(2-benzothiazolyl)alkylamine derivative can be obtained at a high yield by converting a 2-aminothiophenol derivative into its metal salt (e.g. a zinc salt) stable in the air and of no odor, reacting the metal salt with an amino acid-N-carboxyanhydride and conducting cyclization (see Published International Application WO 99/16759). In this method, however, there is a problem that the metal salt (e.g. a zinc salt) generated as a by-product is mixed into a waste water and the disposal of the waste water bears a larger burden; filtration and drying are necessary in taking-out of 2-aminothiophenol derivative metal salt; and so on, thus, the method is complicated and is difficult to employ industrially.

The present invention aims at providing a process for producing a 1-(2-benzothiazolyl)alkylamine derivative, i.e. a substituted alkylamine derivative from a 2-aminothiophenol derivative easily at a satisfactory yield industrially without giving rise to environmental pollution and the like.

DISCLOSURE OF THE INVENTION

The present inventors made a study in order to solve the problems of the prior art. As a result, the present inventors paid attention to making a 2-aminothiophenol derivative acidic and successfully found out that a 2-aminothiophenol derivative can unexpectedly be made acidic with no substantial formation of a disulfide by adding an alkali salt of a 2-aminothiophenol derivative into an acid. The present inventors further found out that while a reaction between a 2-aminothiophenol derivative formed and an amino acid-N-carboxyanhydride requires the presence of an acid, this reaction proceeds with no need of adding an acid newly if the reaction system is maintained acidic when the salt of a 2-aminothiophenol derivative is added into an acid beforehand, and an intended product can be obtained at a high yield; that the reaction is very friendly to the environment because it generates no metal (e.g. zinc)-containing waste water as a by-product and, in the reaction with an amino acid-N-carboxyanhydride, requires no organic solvent; and that the reaction can be conducted in one pot (in one reactor) from the operation of adding a salt of a 2-aminothiophenol derivative into an acid to the completion of a reaction between a 2-aminothiophenol derivative and an amino acid-N-carboxyanhydride and is very easy to carry out, etc. The above findings led to the completion of the present invention.

The above aim has been achieved by the following inventions [1] to [8].

[1] A process for producing a substituted alkylamine derivative represented by the following general formula (3):

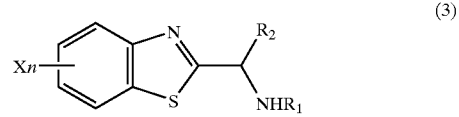

(3)

(wherein X is a halogen atom, an alkyl group, an alkoxy group, a cyano group or a nitro group; n is an integer of 1 to 4; and $R_1$ and $R_2$ are each independently a hydrogen atom or a phenyl group-substituted or unsubstituted alkyl group and may together form a 5- or 6-membered ring), which process comprises adding a salt of a 2-aminothiophenol derivative represented by the following general formula (1):

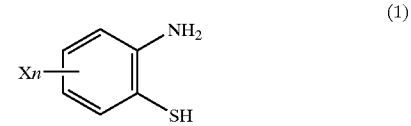

(1)

(wherein X and n have the same definitions as given above) into an acid to allow the system to have a pH of 6 or less and convert the salt into a free 2-aminothiophenol derivative of the general formula (1) and then reacting the 2-aminothiophenol derivative with an amino acid-N- carboxyanhydride represented by the following general formula (2):

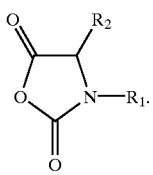

(wherein $R_1$ and $R_2$ each have the same definitions as given above).

[2] A process for producing a substituted alkylamine derivative represented by the following general formula (3):

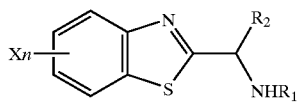

(wherein X is a halogen atom, an alkyl group, an alkoxy group, a cyano group or a nitro group; n is an integer of 1 to 4; and $R_1$ and $R_2$ are each independently a hydrogen atom or a phenyl-substituted or unsubstituted alkyl group and may together form a 5- or 6-membered ring), which process comprises adding a salt of a 2-aminothiophenol derivative represented by the following general formula (1):

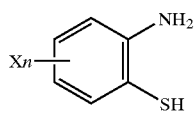

(wherein X and n have the same definitions as given above) into an acid to allow the system to have a pH of 6 or leas and convert the salt into a free 2-aminothiophenol derivative of the general formula (1) and then reacting, in water or a water-organic solvent mixed solvent, the 2-aminothiophenol derivative with an amino acid-N-carboxyanhydride represented by the following general formula (2):

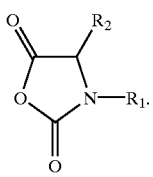

(wherein $R_1$ and $R_2$ each have the same definitions as given above).

[3] A process for producing a substituted alkylamine derivative according to [2], wherein the reaction between the 2-aminothiophenol derivative and the amino acid-N-carboxyanhydride is conducted under an acidic condition.

[4] A process for producing a substituted alkylamine derivative according to [3], wherein the reaction between the 2-aminothiophenol derivative and the amino acid-N-carboxyanhydride is conducted at a pH of 6 or less.

[5] A process for producing a substituted alkylamine derivative according to [1] or [2], wherein the X is a halogen atom.

[6] A process for producing a substituted alkylamine derivative according to [1] or [2], wherein the X is a fluorine atom.

[7] A process for producing a substituted alkylamine derivative according to [1] or [2], wherein the salt of a 2-aminothiophenol derivative is an alkali metal salt of thiophenol.

[8] A process for producing a substituted alkylamine derivative according to [1] or [2], wherein the salt of a 2-aminothiophenol derivative is produced by hydrolyzing a benzothiazole derivative represented by the following general formula (4):

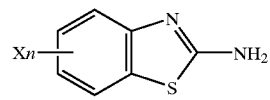

(wherein X and n have the same definitions as given above) with an alkali metal hydroxide.

BEST MODE FOR CARRYING OUT THE INVENTION

The present invention is described in detail below.

In the present process, first, a salt of a 2-aminothiophenol derivative represented by the general formula (1) is added into an acid to convert the salt into a free 2-aminothiophenol derivative of the general formula (1) in the acid. In this case, the pH of the reaction system is preferably controlled at 6 or less. Then, to the reaction mixture obtained is added an amino acid-N-carboxyanhydride represented by the general formula (2) to give rise to a reaction and produce an intended substituted alkylamine derivative represented by the general formula (3). In this case, the reaction system is preferably acidic, and it is more preferable that the reaction is conducted while keeping the reaction system at a pH of 6 or less.

The conversion of the salt of a 2-aminothiophenol derivative into the free 2-aminothiophenol derivative in an acid is appropriately conducted by adding into an acid the salt of a 2-aminothiophenol derivative represented by the general formula (1) (the salt may be an aqueous solution thereof in some cases). This operational procedure characterizes the present process. Meanwhile, addition of an acid to the salt of a 2-aminothiophenol derivative (the salt may be an aqueous solution thereof in some cases) is not preferred because the yield of an intended product is extremely low in the subsequent reaction with an amino acid-N-carboxyanhydride represented by the general formula (2) (see Comparative Example 1 described later).

The 2-aminothiophenol derivative, the salt of which is used as a raw material in the present process, can be any compound represented by the general formula (1). In the formula, X is a hydrogen atom; a halogen atom including chlorine, fluorine, bromine and iodine; a $C_{1-6}$ straight or branched chain alkyl group including methyl group, ethyl group, n-propyl group, isopropyl group, n-butyl group, isobutyl group, sec-butyl group, tert-butyl group, n-pentyl group, n-hexyl group, etc.; an alkoxy group (an alkyl-o-group) wherein the alkyl moiety is the above-mentioned alkyl group; a cyano group; or a nitro group, and n is an integer of 1 to 4.

As examples of the salt of a 2-aminothiophenol derivative represented by the general formula (1), wherein the X and n are as above, there can be mentioned alkali metal salts of 2-aminothiophenol derivatives such as potassium salt of 2-amino-6-fluoro-thiophenol, sodium salt of 2-amino-6-chloro-thiophenol, potassium salt of 2-amino-5-fluoro-thiophenol, sodium salt of 2-amino-5-fluoro-thiophenol, potassium salt of 2-amino-5-bromo-thiophenol, potassium salt of 2-amino-5-chloro-thiophenol, potassium salt of 2-amino-5-methyl-thiophenol, potassium salt of 2-amino-5-methoxy-thiophenol, potassium salt of 2-amino-4-fluoro-thiophenol, potassium salt of 2-amino-4-chloro-thiophenol, potassium salt of 2 amino-4-cyano-thiophenol, sodium salt of 2-amino-4-nitro-thiophenol, potassium salt of 2-amino-4-methyl-thiophenol, potassium salt of 2-amino-4,5-difluoro-thiophenol, potassium salt of 2-amino-3-fluoro-thiophenol, potassium salt of 2-amino-3-bromo-thiophenol, potassium salt of 2-amino-3-chloro-thiophenol, potassium salt of 2-amino-3-methyl-thiophenol and the like; ammonium salts of 2-aminothiophenol derivatives such as ammonium salt of 2-amino-5-fluoro-thiophenol and the like; and organic amine salts of 2-aminothiophenols such as triethylamine salt of 2-amino-5-fluoro-thiophenol and the like.

As the salt of a 2-aminothiophenol derivative, there can also be used salts of metals other than alkali metals, for example, alkaline earth metals and metals of group IIb. As such salts, there can be mentioned, for example, a zinc salt of 2-amino-6-fluoro-thiophenol, a calcium salt of 2-amino-6-fluoro-thiophenol and a barium salt of 2-amino-6-fluoro-thiophenol.

As the salt of a 2-aminothiophenol derivative, alkali metal salts such as sodium salt, potassium salt and the like are generally used industrially and are preferred in view of the yield of intended product.

There is no particular restriction as to the method for obtaining a salt of a 2-aminothiophenol derivative represented by the general formula (1). However, an alkali metal salt of a 2-aminothiophenol derivative can be produced easily at a high yield according to, for example, the method described in JP-A-6-145158 by hydrolyzing a corresponding 2-aminobenzothiazole derivative with an alkali metal hydroxide such as potassium hydroxide or the like as shown in the following reaction formula:

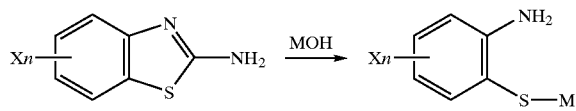

(wherein M is an alkali metal, and X and n have the same definitions as given above) When an alkali metal hydroxide such as sodium hydroxide or the like is used in place of the potassium hydroxide, there can be obtained an alkali metal salt of a 2-aminothiophenol derivative corresponding to that metal.

In the present process, the salt of a 2-aminothiophenol derivative represented by the general formula (1) can be added into an acid in the form of an aqueous solution obtained by hydrolysis of a corresponding 2-aminobenzothiazole derivative, whereby the pH of the reaction system can preferably be made 6 or less. Thus, the present process can offer a simple industrial operation.

In the present process, the acid into which the salt of a 2-aminothlophenol derivative represented by the general formula (1) is added, can be exemplified by mineral acids such as hydrochloric acid, sulfuric acid, hydrobromic acid, phosphoric acid and the like and organic acids such as p-toluenesulfonic acid, methanesulfonic acid, trifluoromethanesulfonic acid and the like. These acids are preferably used as an aqueous solution.

In the present process, the reaction system after addition of the salt of a 2-aminothiophenol derivative represented by the general formula (1) into an acid is controlled at a pH of preferably 6 or less, more preferably 5 or less. Therefore, even when the aqueous solution obtained by this hydrolysis of a 2-aminobenzothiazole derivative is added per se into an acid, the amount of the acid used is determined in view of the amount of the basic component (e.g. alkali metal hydroxide or ammonia, etc.) remaining in the aqueous solution obtained by hydrolysis, the strength of the acid used, etc., whereby the pH of the reaction system is controlled at the above level. The temperature at which the salt of a 2-aminothiophenol derivative represented by the general formula (1) is added into an acid, can be −20 to 60° C., preferably −5 to 40° C.

In a specific case of using, for example, a potassium salt of a 2-aminothiophenol derivative and concentrated hydrochloric acid, the pH of the reaction system is controlled at a desired level by using 1 mole of the potassium salt of a 2-aminothiophenol derivative and 1 mole or more, preferably 2 moles or more of hydrochloric acid.

In the subsequent reaction of a free 2-aminothiophenol derivative of the general formula (1) with an amino acid-N-carboxyanhydride represented by the general formula (2), the aqueous solution obtained by addition of the salt of a 2-aminothiophenol derivative represented by the general formula (1) into an acid can be used per se.

The amino acid-N-carboxyanhydride represented by the general formula (2), used in the present process can be any compound represented by the general formula (2). The amino acid moiety of the compound represented by the general formula (2) may be an optically active compound, a mixture of any proportions of different optically active compounds, or a racemic modification. With respect to the stereochemistry of the substituted alkylamine derivative obtained by the present process, the configuration and optical purity of the amino acid used as a starting material in the production of the amino acid-N-carboxyanhydride of the general formula (2) are kept.

In the general formula (2), $R_1$ and $R_2$ are a hydrogen atom or a phenyl group-substituted or unsubstituted alkyl group. The alkyl group may be a $C_{1-6}$ straight or branched chain alkyl group and can be specifically exemplified by methyl group, ethyl group, n-propyl group, isopropyl group, n-butyl group, isobutyl group, sec-butyl group, tert-butyl group, n-pentyl group and n-hexyl group. As the phenyl group-substituted alkyl group, a benzyl group, for example, can be mentioned. $R_1$ and $R_2$ may together form a triethylene group, a tetraethylene group or the like, and may combine with the amino acid skeleton to form a ring.

As the amino acid-N-carboxyanhydride represented by the general formula (2), having such $R_1$ and $R_2$, there can be mentioned, for example, glycine-N-carboxyanhydride, DL-alanine-N-carboxyanhydride, D-alanine-N-carboxyanhydride, L-alanine-N-carboxyanhydride, DL-valine-N-carboxyanhydride, D-valine-N-carboxyanhydride, L-valine-N-carboxyanhydride, DL-phenylalanine-N-carboxyanhydride, D-phenylalanine-N-carboxy-anhydride, L-phenylalanine-N-carboxyanhydride, DL-phenylglycine-N-carboxyanhydride, D-phenylglycine-N-carboxyanhydride, L-phenylglycine-N-carboxyanhydride, DL-proline-N-carboxyanhydride, D-proline-N-carboxyanhydride, L-proline-N-carboxyanhydride, DL-alanine-N-methyl-N-carboxyanhydride, D-alanine-N-methyl-N-carboxyanhydride and L-alanine-N-methyl-N-carboxyanhydride.

The amino acid-N-carboxyanhydride used may be a dried product, or a product wetted with, for example, the reaction solvent (e.g. tetrahydrofuran) used in its production or the organic solvent used in its recrystallization, or a solution dissolved in tetrahydrofuran, acetonitrile or the like.

There is no particular restriction as to the method for obtaining the amino acid-N-carboxyanhydride represented by the general formula (2). The compound can be produced easily according to, for example, the method described in J. Org. Chem., Vol. 53, p. 836 (1988) by reacting a corresponding amino acid derivative with phosgene.

In the reaction between the 2-aminothiophenol derivative represented by the general formula (1) and the amino acid-N-carboxyanhydride represented by the general formula (2), the amount of the amino acid-N-carboxyanhydride used is 0.7 to 3 moles, preferably 1.0 to 1.2 moles per mole of the 2-aminothiophenol derivative represented by the general formula (1).

In the reaction, an acid may be added so as to control the pH of the reaction system at 6 or less. The acid used therefor can be exemplified by mineral acids such as hydrochloric acid, sulfuric acid, hydrobromic acid, phosphoric acid and the like, and organic acids such as p-toluenesulfonic acid, methanesulfonic acid, trifluoromethanesulfonic acid and the like. The amount of the acid used therefor may be any amount as long as the pH of the reaction system can be controlled preferably at 6 or less, more preferably at 5 or less.

In the reaction, an aqueous solution of the 2-aminothiophenol derivative may be used per se as a solvent, or an organic solvent miscible with water may be added.

As the organic solvent miscible with water, used in the reaction, there can be mentioned, for example, ether type organic solvents such as tetrahydrofuran, 1,4-dioxane and the like; nitrile type organic solvents such as acetonitrile and the like; amide type aprotic polar solvents including N,N-dimethylformamide, N,N-dimethylacetamide, N,N-diethylacetamide, 1,3-dimethyl-2-imidazolidinone, 1-methyl-2-pyrrolidone, 1,3-dimethyl-3,4,5,6-tetrahydro-2 (1H)-pyrimidinone, 1,1,3,3-tetramethylurea, etc.; sulfur-containing aprotic polar solvents including sulfolane, dimethyl sulfoxide, etc.; and hexamethylphosphoric triamide. Of these, ether type organic solvents such as tetrahydrofuran and the like and nitrile type organic solvents such as acetonitrile and the like are preferred.

These organic solvents may be used singly or in admixture of two or more kinds. When the melting point of the solvent used is higher than the reaction temperature, their mixed use with, for example, an amide type aprotic polar solvent is preferred.

The amount of the organic solvent used is 0 to 20,000 ml, preferably 0 to 1,000 ml per mole of the 2-aminothiophenol derivative represented by the general formula (1).

Incidentally, when the organic solvent miscible with water is replaced by a no-polarity or low-polarity organic solvent immiscible with water, for example, chlorobenzene, a phase transfer catalyst is used, and a two-phase reaction is conducted, such a reaction is disadvantageous in the yield; therefore, the significance of adopting such a reaction is substantially low.

The temperature of the reaction is −50 to 60° C., preferably −30 to 40° C. The time of the reaction is ordinarily 12 hours or less. The reaction is conducted by adding an amino acid-N-carboxyanhydride to a solution of the 2-aminothiophenol derivative represented by the general formula (1) at a predetermined temperature at atmospheric pressure and stirring the mixture. No pressure application is required ordinarily.

The reaction mixture after the reaction is treated with an alkali as necessary, followed by extraction with an organic solvent, whereby an intended substituted alkylamine derivative can be isolated easily. By adding an acid (a mineral acid or an organic acid), a salt of an intended substituted alkylamine derivative can be isolated. The mineral acid used therefor can be exemplified by hydrochloric acid, sulfuric acid, hydrobromic acid and phosphoric acid; the organic acid can be exemplified by p-toluenesulfonic acid, methanesulfonic acid and trifluoromethanesulfonic acid.

After the completion of the reaction, the intended substituted alkylamine derivative is in the form of a salt with an acid. Therefore, when the salt (for example, a p-toluenesulfonic acid salt of an intended product) is precipitated from the reaction system owing to, for example, salting out, the salt can be easily isolated by filtration or the like. Incidentally, it is also possible to easily isolate an intended substituted alkylamine derivative by adding, to the reaction mixture after the reaction, an aqueous solution of an alkali metal hydroxide (e.g. sodium hydroxide or potassium hydroxide) to make free the amino group of substituted alkylamine derivative and then conducting extraction with an organic solvent. When the intended substituted alkylamine derivative forms a salt with an acid and is in a dissolved state, it is possible to take out the sale as an aqueous solution of the salt or as a solution of the salt dissolved in a water organic solvent mixture.

As mentioned previously, with respect to the stereochemistry of the substituted alkylamine derivative, the reaction proceeds while the configuration and optical purity of the amino acid used as a starting material in the production of an amino acid-N-carboxyanhydride are being kept.

As the substituted alkylamine derivative represented by the general formula (3), produced by the present process, there can be mentioned, for example, (6-fluoro-2-benzothiazolyl)methylamine, (RS)-1-(2-benzothiazolyl) ethylamine, (R)-1-(2-benzothiazolyl)ethylamine, (S)-1-(2-benzothiazolyl)ethylamine, (RS)-1-(6-fluoro-2-benzothiazolyl)ethylamine, (R)-1-(6-fluoro-2-benzothiazolyl)ethylamine, (S)-1-(6-fluoro-2-benzothiazolyl)ethylamine, (R)-1-(4-chloro-2-benzothiazolyl)ethylamine, (R)-1-(5-chloro-2-benzothiazolyl)ethylamine, (R) 1-(6-chloro-2-benzothiazolyl)ethylamine, (R)-1-(6-bromo-2-benzothiazolyl)ethylamine, (R)-1-(4-methyl-2-benzothiazolyl)ethylamine, (R)-1-(6-methyl-2-benzothiazolyl)ethylamine, (R)-1-(6-methoxy-2-benzothiazolyl)ethylamine, (R)-1-(5-cyano-2-benzothiazolyl)ethylamine, (R)-1-(5-nitro-2-benzothiazolyl)ethylamine, (RS)-1-(6-fluoro-2-benzothiazolyl)-2-methylpropylamine, (R)-1-(6-fluoro-2-benzothiazolyl)-2-methylpropylamine, (S)-1-(6-fluoro-2-benzothiazolyl)-2-methylpropylamine, (RS)-1-(4-methyl-2-benzothiazolyl)-2-methylpropylamine, (R)-1-(4-methyl-2-benzothiazolyl)-2-methylpropylamine, (S)-1-(4-methyl-2-benzothiazolyl)-2-methylpropylamine, (RS)-1-(6-fluoro-2-benzothiazolyl)benzylamine, (R)-1-(6-fluoro-2-benzothiazolyl)benzylamine, (S)-1-(6-fluoro-2-benzothiazolyl)benzylamine, (RS)-2-(6-fluoro-2-benzothiazolyl)pyrrolidine, (R)-2-(6-fluoro-2-benzothiazolyl)pyrrolidine and (S)-2-(6-fluoro-2-benzothiazolyl)pyrrolidine.

The substituted alkylamine derivative represented by the general formula (3), obtained by the present process is very useful as an intermediate for production of fungicide for agricultural and horticulture applications (see JP-A-8-176115).

The present process is hereinafter described more specifically by way of Examples.

EXAMPLE 1

40 ml of water and 30 g (0.296 mole) of 36% hydrochloric acid were placed in a 300-ml flask as a reactor, and cooled to 3° C. Thereto was dropwise added, at 2 to 5° C. with stirring, 48.0 g (0.056 mole) of an aqueous solution of a potassium salt of 2-amino-5-fluororothophenol, followed by stirring for 1 hour. The system had a pH of 5.23. Thereto were added 9.7 g (0.051 mole) of p-toluenesulfonic acid monohydrate and 15 ml of tetrahydrofuran, followed by stirring for 30 minutes. Thereto was added 8.1 g (0.055 mole) of D-alanine-N-carboxyanhydride (purity: 78.3%) at 0° C. The resulting mixture was aged at 15 to 20° C. for 18 hours. The resulting crystals were collected by filtration and dried at 60° C. to obtain 16.6 g of a p-toluenesulfonate of [2-(6-fluorobenzothiazolyl)]ethylamine (purity: 93.5%) (the yield was 82.8% relative to the potassium salt of 2-amino-5-fluorothiophenol).

Comparative Example 1

48.2 g (0.056 mole) of an aqueous solution of a potassium salt of 2-amino-5-fluorothiophenol was placed in a 300-ml flask as a reactor, and cooled to 1° C. Thereto was dropwise added 72.0 g (0.296 mole) of 15% hydrochloric acid at 0 to 5° C. with stirring, followed by stirring for 1 hour. The system had a PH of 5.40. Thereto were added 9.7 g (0.051 mole) of p-toluenesulfonic acid monohydrate and 15 ml of tetrahydrofuran, followed by stirring for 30 minutes. Thereto was added 8.1 g (0.055 mole) of D-alanine-N-carboxyanhydride (purity: 78.3%) at 0° C. The resulting mixture was aged at 15 to 20° C. for 18 hours. The resulting crystals were collected by filtration and dried at 60° C. to obtain 12.2 g of a p-toluenesulfonate of [2-(6-fluorobenzothiazolyl)]ethylamine (purity: 76.5%) (the yield was 45.2% relative to the potassium salt of 2-amino-5-fluorothiophenol).

EXAMPLE 2

80 ml of water and 60 g (0.592 mole) of 36% hydrochloric acid were placed in a 500-ml flask as a reactor, and cooled to 2° C. Thereto was dropwise added, at 0 to 5° C. with stirring, 96.1 g (0.112 mole) of an aqueous solution of a potassium salt of 2-amino-5-fluorothiophenol, followed by stirring for 1 hour. The system had a pH of 5.02. Thereto were added 19.4 g (0.102 mole) of p-toluenesulfonic acid monohydrate and 25 ml of tetrahydrofuran, followed by stirring for 30 minutes. Thereto was added 16.2 g (0.110 mole) of D-alanine-N-carboxyanhydride (purity: 78.3%) at 0° C. The resulting mixture was aged at 15 to 20° C. for 18 hours. The resulting crystals were collected by filtration and dried at 60° C. to obtain 33.9 g of a p-toluenesulfonate of [2-(6-fluorobenzothiazolyl)]ethylamine (purity: 92.04%) (the yield was 75.6% relative to the potassium salt of 2-amino-5-fluorothiophenol).

EXAMPLE 3

230.4 g of water and 172.8 g (1.706 mole) of 36% hydrochloric acid were placed in a 2-liter flask as a reactor, and cooled to 3° C. Thereto was dropwise added 276.5 g (0.315 mole) of an aqueous solution of a potassium salt of 2-amino-5-fluorothiophenol at 0 to 5° C. with stirring, followed by stirring for 1 hour. Further, 15.8 g of 50% potassium hydroxide was added dropwise to adjust the system pH to 4.95. Aging was conducted for 1 hour. Then, 56.4 g (0.296 mole) of p-toluenesulfonic acid monohydrate was added, followed by aging at 3° C. for 30 minutes. Thereto was dropwise added, at 16 to 19° C., a beforehand prepared solution of D-alanine-N-carboxyanhydride (46.8 g, purity: 78.3%, 0.318 mole) dissolved in tetrahydrofuran (73 ml). Aging was conducted at 15 to 20° C. for 18 hours. The resulting crystals were collected by filtration and dried at 60° C. to obtain 96.6 g of a p-toluenesulfonate of [2-(6-fluorobenzothiazolyl)]ethylamine (purity: 93.76%) (the yield was 78.0% relative to the potassium salt of 2 amino-5-fluorothiophenol).

EXAMPLE 4

80 ml of water and 60 g (0.592 mole) of 36% hydrochloric acid were placed in a 500-ml flask as a reactor, and cooled to 0 to 2° C. Thereto was dropwise added, at 0 to 5° C. with stirring, 96.0 g (0.112 mole) of an aqueous solution of a potassium salt of 2-amino-5-fluorothiophenol. The resulting mixture had a pH of 0.90. Further, 20.0 g (0.105 mole) of p-toluenesulfonic acid monohydrate was added. Thereto was dropwise added, at 16 to 20° C., a solution of D-alanine-N-carboxyanhydride (16.7 g, purity: 78.3%, 0.318 mole) dissolved in tetrahydrofuran (30 ml) (the solution was beforehand prepared at 16 to 20° C.). Aging was conducted at 15 to 20° C. for 4 hours. The resulting crystals were collected by filtration and dried at 60° C. to obtain 31.5 g of a p-toluenesulfonate of [2-(6-fluorobenzothiazolyl)] ethylamine (purity: 98.95%) (the yield was 75.5% relative to the potassium salt of 2-amino-5-fluorothiophenol).

EXAMPLE 5

Reactions were conducted in the same scale and operation as in Example 4 except that the reaction system after the dropwise addition of the aqueous solution of a potassium salt of 2-amino-5-fluorothiophenol was adjusted to a pH of 3.69, whereby was obtained 30.6 g of a p-toluenesulfonate of [2-(6-fluorobenzothiazolyl)]ethylamine (purity: 98.84%) (the yield was 73.1% relative to the potassium salt of 2-amino-5-fluorothiophenol).

Comparative Example 2

Reactions were conducted in the same scale and operation as in Example 4 except that the reaction system after the dropwise addition of the aqueous solution of a potassium salt of 2-amino-5-fluorothiophenol was adjusted to a pH of 7.03 and the aging time was changed to 18 hours, whereby was obtained 27.0 g of a p-toluenesulfonate of [2-(6-fluorobenzothiazolyl)]ethylamine (purity: 19.59 1) (the yield was 12.8% relative to the potassium salt of 2-amino-5-fluorothiophenol).

EXAMPLE 6

80 ml of water and 60 g (0.592 mole) of 36% hydrochloric acid were placed in a 500-ml flask as a reactor, and cooled to 0° C. Thereto was dropwise added, at 0 to 5° C. with stirring, 96.0 g (0.112 mole) of an aqueous solution of a potassium salt of 2-amino-5-fluorothiophenol, followed by aging for 1 hour. The system had a pH of 1.26. Thereto was dropwise added, at 15 to 20° C., a solution of D-alanine-N-carboxyanhydride (16.7 g, purity: 78.3%, 0.318 mole) dissolved in 30 ml of acetonitrile (the solution was prepared beforehand at 15 to 20° C.). Aging was conducted at 15 to 20° C. for 3 hours. The resulting system was subjected to phase separation at 40° C. two times with 50 ml of toluene. From the lower layer was obtained an aqueous solution (concentration: 8.96%) containing 221.5 g of [2-(6-fluorobenzothiazolyl)]ethylamine hydrochloride. The yield was 90.3% relative to the potassium salt of 2-amino-5-fluorothiophenol.

EXAMPLE 7

80 ml of water and 60 g (0.592 mole) of 36% hydrochloric acid were placed in a 500-ml flask as a reactor, and cooled to 0° C. Thereto was dropwise added, at 0 to 5° C. with stirring, 96.0 g (0.112 mole) of an aqueous solution of a potassium salt of 2-amino-5-fluorothiophenol, followed by aging for 1 hour. The system had a pH of 1.54. Thereto was dropwise added, at 15 to 20° C., a solution of D-alanine-N-carboxyanhydride (16.7 g, purity: 78.3%, 0.318 mole) dissolved in 30 ml of tetrahydrofuran (the solution was prepared beforehand at 15 to 20° C.). Aging was conducted at 40° C. for 2 hours. The resulting system was subjected to phase separation at 40° C. two times with 50 ml of toluene. From the lower layer was obtained an aqueous solution (concentration: 10.42%) containing 211.2 g of [2-(6-fluorobenzothiazolyl)]ethylamine hydrochloride. The yield was 99.9% relative to the potassium salt of 2-amino-5-fluorothiophenol.

EXAMPLE 8

In a 2,000-ml flask as a reactor were placed 166.7 g of water, 589.3 g of a 50% aqueous potassium hydroxide solution (5.25 moles as KOH) and 168.2 g (1.00 mole) of 6-fluoro-2-aminobenzothiazole. They were heated, aged for 8 hours with refluxing at 113 to 115° and then cooled to 40° C. The resulting mixture was washed with 311 g of toluene and then subjected to phase separation to obtain 904.0 g of an aqueous solution of a potassium salt of 2-amino-5-fluorothiophenol (concentration: 20%, yield: 99.7%). This aqueous solution of a potassium salt of 2-amino-5-fluorothiophenol can be used for production of a p-toluenesulfonate of [2-(6-fluorobenzothiazolyl)]ethylamine or an aqueous solution of [2-(6-fluorobenzothiazolyl)]ethylamine hydrochloride, according to the description in Example 1 to Example 7.

EXAMPLE 9

80 ml of water and 60 g (0.592 mole) of 36% hydrochloric acid were placed in a 300-ml flask as a reactor, and cooled to 3° C. Thereto was dropwise added, at 2 to 5° C. with stirring, 96 g (0.112 mole) of an aqueous solution of a potassium salt of 2-amino-5-fluorothiophenol, followed by stirring for 1 hour. The system had a pH of 5.23. Thereto were added 20 g (0.105 mole) of p-toluenesulfonic acid monohydrate and 30 ml of tetrahydrofuran, followed by stirring for 30 minutes. Thereto was added 16.7 g (0.114 mole) of D-alanine-N-carboxyanhydride (purity: 78.3%) at 0° C. The resulting mixture was aged at 15 to 20° C. for 18 hours. The resulting crystals were collected by filtration and dried at 60° C. to obtain 36.0 g of a p-toluenesulfonate of [2-(6-fluorobenzothiazolyl)]ethylamine (purity: 95.2%) (the yield was 82.8% relative to the potassium salt of 2-amino-5-fluorothiophenol).

EXAMPLE 10

80 ml of water and 60 g (0.592 mole) of 36% hydrochloric acid were placed in a 500-ml flask as a reactor, and cooled to 2° C. Thereto was dropwise added, at 0 to 5° C. with stirring, 96.1 g (0.112 mole) of an aqueous solution of a potassium salt of 2-amino-5-fluorothiophenol, followed by stirring for 1 hour. The system had a pH of 5.02. Thereto were added 19.4 g (0.102 mole) of p-toluenesulfonic acid monohydrate and 25 ml of tetrahydrofuran, followed by stirring for 30 minutes. Thereto was added 16.2 g (0.110 mole) of D-alanine-N-carboxyanhydride (purity: 78.3%) at 0° C. The resulting mixture was aged at 15 to 20° C. for 18 hours. The resulting crystals were collected by filtration and dried at 60° C. to obtain 30.9 g of a p-toluenesulfonate of [2-(6-fluorobenzothiazolyl)]ethylamine (purity: 92%) (the yield was 75.6% relative to the potassium salt of 2-amino-5-fluorothiophenol).

EXAMPLE 11

80 ml of water and 60 g (0.592 mole) of 36% hydrochloric acid were placed in a 500-ml flask as a reactor, and cooled to 0 to 2° C. Thereto was dropwise added, at 0 to 5° C. with stirring, 96.0 g (0.112 mole) of an aqueous solution of a potassium salt of 2-amino-5-fluorothiophenol. The system had a pH of 0.90. Thereto was added 20.0 g (0.105 mole) of p-toluenesulfonic acid monohydrate. Then, a solution of D-alanine-N-carboxyanhydride (16.7 g, purity: 78.3%, 0.318 mole) dissolved in tetrahydrofuran (30 ml) (the solution was beforehand prepared at 16 to 20° C.) was added dropwise at 16 to 20° C. Aging was conducted at 15 to 20° C. for 4 hours. The resulting crystals were collected by filtration and dried at 60° C. to obtain 31.5 g of a p-toluenesulfonate of [2-(6-fluorobenzothiazolyl)]ethylamine (purity: 98.95%) (the yield was 75.5% relative to the potassium salt of 2-amino-5-fluorothiophenol).

EXAMPLE 12

80 ml of water and 72 g (0.711 mole) of 36% hydrochloric acid were placed in a 500-ml flask as a reactor, and cooled to 0° C. Thereto was dropwise added, at 0 to 5° C. with stirring, 96.0 g (0.112 mole) of an aqueous solution of a potassium salt of 2-amino-5-fluorothiophenol, followed by aging for 1 hour. The system had a pH of 1.26. Thereto was dropwise added, at 15 to 20° C., a solution of D-alanine-N-carboxyanhydride (16.7 g, purity: 78.3%, 0.318 mole) dissolved in 30 ml of acetonitrile (the solution was prepared beforehand at 15 to 20° C.). Aging was conducted at 15 to 20° C. for 3 hours. The resulting system was subjected to phase separation at 40° C. two times with 50 ml of toluene. From the lower layer was obtained an aqueous solution (concentration: 8.96%) containing 263.0 g of [2-(6-fluorobenzothiazolyl)]ethylamine hydrochloride. The yield was 90.3% relative to the potassium salt of 2-amino-5-fluorothiophenol.

EXAMPLE 13

80 ml of water and 72 g (0.711 mole) of 36% hydrochloric acid were placed in a 500-ml flask as a reactor, and cooled to 0° C. Thereto was dropwise added, at 0 to 5° C. with stirring, 96.0 g (0.112 mole) of an aqueous solution of a potassium salt of 2-amino-5-fluorothiophenol, followed by aging for 1 hour. The system had a pH of 1.54. Thereto was dropwise added, at 15 to 20° C., a solution of D-alanine-N-carboxyanhydride (16.7 g, purity: 78.3%, 0.318 mole) dissolved in 30 ml of tetrahydrofuran (the solution was prepared beforehand at 15 to 20° C.). Aging was conducted at 40° C. for 2 hours. The resulting system was subjected to phase separation at 40° C. two times with 50 ml of toluene. From the lower layer was obtained an aqueous solution (concentration: 10.42%) containing 251.1 g of [2-(6-fluorobenzothiazolyl)]ethylamine hydrochloride. The yield was 99.9% relative to the potassium salt of 2-amino-5-fluorothiophenol.

Industrial Applicability

The present invention provides a process for producing a substituted alkylamine derivative or an acid addition salt both useful as an intermediate for medicine or agrochemical, from a 2-aminothiophenol derivative, at a high yield industrially. In the present process, even a fluorine-substituted 2-aminothiophenol derivative (such a compound forms a disulfide easily) can be used; since no metal (e.g. zinc) salt is mixed into the waste water, the burden of waste water disposal is small; in taking-out of metal salt of 2-aminothiophenol derivative, filtration and drying are not necessarily required; therefore, the present process is very useful as a process for industrial production of a substituted alkylamine derivative represented by the general formula (3) or an acid addition salt thereof.

What is claimed is:

1. A process for producing a substituted alkylamine derivative represented by the following formula (3):

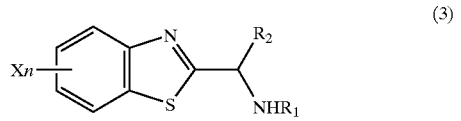
(3)

wherein X is a halogen atom, an alkyl group, an alkoxy group, a cyano group or a nitro group; n is an integer of 1 to 4; and $R_1$ and $R_2$ are each independently a hydrogen atom or a phenyl group-substituted or unsubstituted alkyl group and may together form a 5- or 6-membered ring, which process comprises adding a salt of a 2-aminothiophenol derivative represented by the following formula (1):

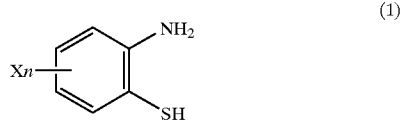
(1)

wherein X and n have the same definitions as given above, into an acid while controlling the pH of the system to 6 or less thereby converting the salt into a free 2-aminothiophenol derivative of the formula (1) and then reacting the 2-aminothiophenol derivative with an amino acid-N-carboxyanhydride represented by the following formula (2):

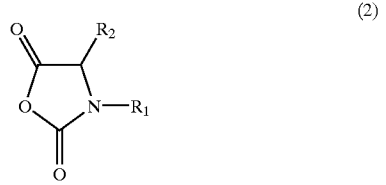
(2)

wherein $R_1$ and $R_2$ each have the same definitions as given above.

2. A process for producing a substituted alkylamine derivative represented by the following formula (3):

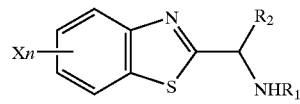
(3)

wherein X is a halogen atom, an alkyl group, an alkoxy group, a cyano group or a nitro group; n is an integer of 1 to 4; and $R_1$ and $R_2$ are each independently a hydrogen atom or a phenyl group-substituted or unsubstituted alkyl group and may together form a 5- or 6-membered ring, which process comprises adding a salt of a 2-aminothiophenol derivative represented by the following formula (1):

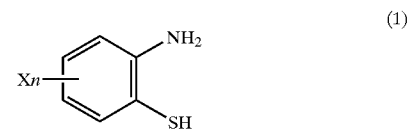
(1)

wherein X and n have the same definitions as given above, into an acid while controlling the pH of the system to 6 or less thereby converting the salt into a free 2-aminothiophenol derivative of the formula (1) and then reacting, in water or a water-organic solvent mixture, the 2-aminothiophenol derivative with an amino acid-N-carboxyanhydride represented by the following formula (2):

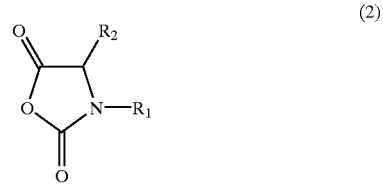
(2)

wherein $R_1$ and $R_2$ each have the same definitions as given above.

3. A process for producing a substituted alkylamine derivative according to claim 2, wherein the reaction between the 2-aminothiophenol derivative and the amino acid-N-carboxyanhydride is conducted under an acidic condition.

4. A process for producing a substituted alkylamine derivative according to claim 3, wherein the reaction between the 2-aminothiophenol derivative and the amino acid-N-carboxyanhydride is conducted at a pH of 6 or less.

5. A process for producing a substituted alkylamine derivative according to claim 1, wherein the X is a halogen atom.

6. A process for producing a substituted alkylamine derivative according to claim 1, wherein the X is a fluorine atom.

7. A process for producing a substituted alkylamine derivative according to claim 1, wherein the salt of a 2-aminothiopehenol derivative is an alkali metal salt of thiophenol.

8. A process for producing a substituted alkylamine derivative according to claim 1, wherein the alkali metal salt of a 2-aminothiophenol derivative is produced by hydrolyzing a benzothiazole derivative represented by the following general formula (4):

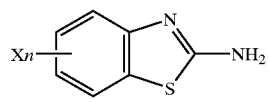

(4)

wherein X and n have the same definitions as give above, with an alkali metal hydroxide.

9. A process for producing a substituted alkylamine derivative according to claim 2, wherein the X is a halogen atom.

10. A process for producing a substituted alkylamine derivative according to claim 2, wherein the X is a fluorine atom.

11. A process for producing a substituted alkylamine derivative according to claim 2, wherein the salt of a 2-aminothiopehenol derivative is an alkali metal salt of thiophenol.

12. A process for producing a substituted alkylamine derivative according to claim 2, wherein the alkali metal salt of a 2-aminothiophenol derivative is produced by hydrolyzing a benzothiazole derivative represented by the following general formula (4):

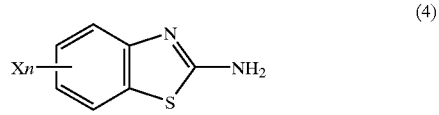

(4)

wherein X and n have the same definitions as give above, with an alkali metal hydroxide.

* * * * *